(12) United States Patent
Shuangshuang et al.

(10) Patent No.: US 8,647,277 B2
(45) Date of Patent: Feb. 11, 2014

(54) METHODS AND APPARATUS FOR HPRF DOPPLER ULTRASONIC IMAGING

(75) Inventors: Li Shuangshuang, Shenzhen (CN); Li Lei, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 392 days.

(21) Appl. No.: 13/007,437

(22) Filed: Jan. 14, 2011

(65) Prior Publication Data

US 2011/0178406 A1    Jul. 21, 2011

(30) Foreign Application Priority Data

Jan. 21, 2010    (CN) .......................... 2010 1 0044456

(51) Int. Cl.
*A61B 8/00* (2006.01)
(52) U.S. Cl.
USPC ....................................................... 600/453
(58) Field of Classification Search
None
See application file for complete search history.

(56) References Cited

U.S. PATENT DOCUMENTS

| | | | |
|---|---|---|---|
| 5,961,462 A | | 10/1999 | Loupas et al. |
| 6,447,455 B2 | | 9/2002 | Bang et al. |
| 2007/0164898 A1 | | 7/2007 | Pan et al. |

FOREIGN PATENT DOCUMENTS

| | | |
|---|---|---|
| CN | 1298688 A | 6/2001 |
| CN | 101647715 A | 2/2010 |
| JP | 2007301180 A | 11/2007 |

*Primary Examiner* — Unsu Jung
*Assistant Examiner* — Saurel J Selkin
(74) *Attorney, Agent, or Firm* — Kory D. Christensen; Stoel Rives LLP

(57) ABSTRACT

A method for High Pulse Repeat Frequency (HPRF) Doppler ultrasonic imaging comprises: collecting parameters including a selected PRF level, real sample volume depth and sampling gate size; setting a selectable PRF range according to a standard PRF value corresponding to the selected PRF level; evaluating each PRF successively selected from the selectable PRF range with a preset step; and taking the PRF with best evaluation as the best PRF of the selected PRF level to be used in ultrasonic pulses transmission.

16 Claims, 4 Drawing Sheets

(a)

(b)

METHODS AND APPARATUS FOR HPRF DOPPLER ULTRASONIC IMAGING

CROSS-REFERENCE TO RELATED APPLICATIONS

This application claims the benefit of Chinese Patent Application No. 201010044456.X, filed on Jan. 21, 2010, which is incorporated herein by reference in its entirety.

TECHNICAL FIELD

This disclosure relates to pulsed wave spectral Doppler imaging and, in particular, to High Pulse Repeat Frequency (HPRF) Doppler ultrasonic imaging.

DETAILED DESCRIPTION

Figure 1:
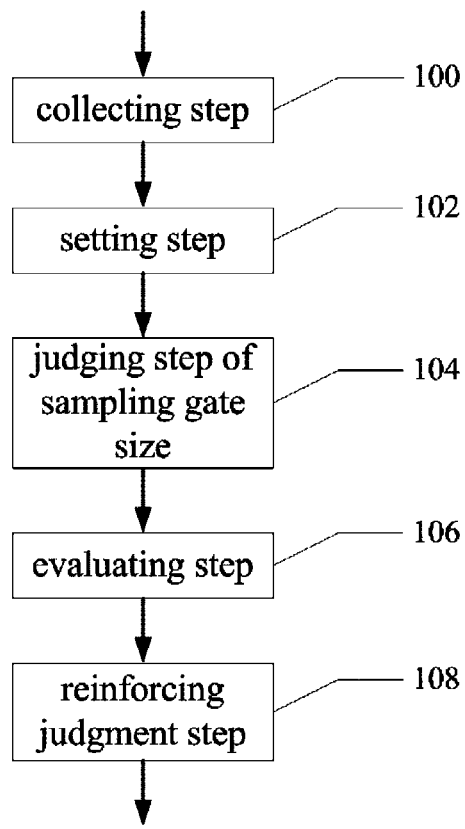
FIG. 1 is a flowchart of a method for HPRF Doppler ultrasonic imaging.

During the process of pulsed wave spectral Doppler imaging (hereinafter "PW imaging") in a medical ultrasonic imaging system, to detect the Doppler frequency shift, the ultrasonic front-end emits an ultrasonic pulsed signal at regular intervals into human tissue. In conventional PW imaging, to ensure that speed information is accurately obtained at the target location, i.e., Sample Volume Depth ("SVD"), the Pulse Repeat Interval ("PRI") will be limited by the SVD. That is, the neighbor PRI should be larger than the time required for the ultrasonic wave to go from the probe to the SVD and back to the probe. If the next ultrasonic wave is sent before the previous ultrasonic wave returns back to the probe, the information received will be mixed with speed information from another target location. The pulse repeat frequency ("PRF"), i.e., the reciprocal of PRI, determines the maximum speed range recognized by the current Doppler frequency. In some cases, in a large arterial vessel, for example, the velocity of blood flow is higher and needs a higher PRF. However, if the location of the vessel is deeper, the time for the ultrasonic signal to be sent and received is longer, so larger PRI or lower PRF is needed, and conventional PW imaging fails to meet this requirement.

To solve these problems, high PRF (HPRF) pulsed wave spectral Doppler imaging is used. Higher PRF is utilized so that the echo signal of the nth emission pulse comes back to the probe at the same time with those of the (n−1)th, (n−2)th, . . . , (n−m+1)th emission pulse. Thus, the received echo signal contains the echo information of the emission pulse of the former m times. Therefore, the received spectral information may come from m depth positions. Except for the real target position SVD, the other m−1 depth positions are referred to as virtual sample positions, and the original SVD is referred to as the real sample position. In the actual use, the user determines which depth position the received velocity information comes from according based on experience. For example, if a certain sample position has no blood flow or tissue movement, the received large velocity won't be from the sample position. The depth relation between m−1 virtual sample position and the real sample position is as follow:

$$\frac{2 * SVD_{real}}{c} - \frac{2 * SVD_{dummy}}{c} = \frac{k}{PRF}, k = 1, 2, \ldots, m-1$$

where c is the velocity of ultrasonic wave in human tissue.

According to the HPRF technology, the PRF is fixed level preset in the system. The Doppler spectrogram associated with each PRF is acquired, after which the system calculates one or more corresponding virtual sample position(s) using the above formula so that user can determine where the received spectral information comes from.

The shortcoming of existing HPRF technology is that the aforesaid PRF is a preset fixed level and only one value is used in emission and reception in actual use. However, the position of the real sample is determined by the target blood vessel or tissue of the target patient, and the position is variable. In some real sample positions, the PRF may lead to the time of the target signal to the probe being too near to the pulse emission time, such that the received target spectral SNR will be reduced, and the judgment of acquiring target velocity information will be effected. That is, to some real sample positions, which are given arbitrarily, the preset PRFs might be not optimal or even not advisable.

The present disclosure provides a method and apparatus for improving the performance of HPRF Doppler ultrasonic imaging by means of transmitting with the best PRF, wherein the best PRF is calculated by a PRF level selected by the user and a sampling gate position.

According to the one aspect of the disclosure, a method for improving HPRF performance in Doppler ultrasonic imaging includes collecting parameters selected by a user through an interface, the parameters including a selected PRF level, a real sample volume depth, and a sampling gate size; setting a selectable PRF range according to the standard PRF value corresponding to the selected PRF level; evaluating each PRF successively selected from the selectable PRF range with a preset step; and selecting the PRF with best evaluation as the best PRF of the selected PRF level, which is then utilized in transmitting ultrasonic pulses.

According to another aspect, an apparatus for improving HPRF performance in Doppler ultrasonic imaging includes: a collecting unit configured for collecting parameters selected by a user through an interface, the parameters including the selected PRF level, real sample volume depth and sampling gate size; a setting unit configured for setting an selectable PRF range according to the standard PRF value corresponding to the selected PRF level; and an evaluating unit configured for evaluating each PRF successively selected from the selectable PRF range with a preset step; wherein the PRF with best evaluation is taken as the best PRF of the selected PRF level and utilized in transmitting ultrasonic pulses.

In one embodiment, the ultrasonic pulse with the best PRF is emitted in real time, wherein the best PRF is calculated with the PRF level and the SVD chosen by user, and the SNR of the Doppler spectrogram is enhanced under HPRF mode, thus the imaging effect of the Doppler spectrum is improved.

Referring to FIG. 1, a method for HPRF Doppler ultrasonic imaging includes a collecting step 100, a setting step 102, and an evaluating step 106. In other embodiments, the method may optionally include a judging step of sampling gate size 104 and/or a reinforcing judgment step 108.

Figure 2:
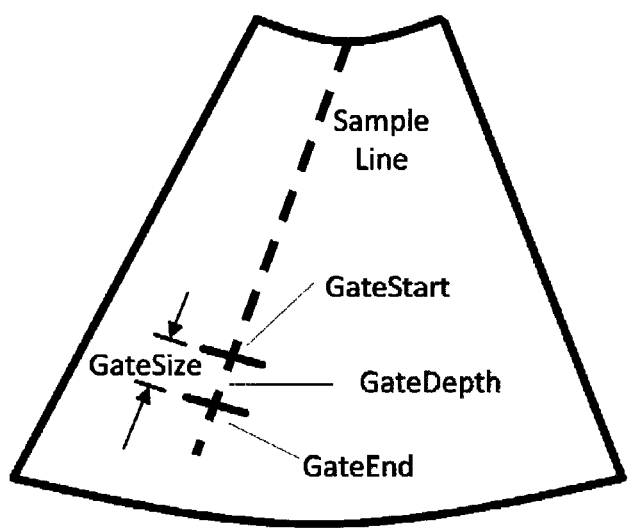
FIG. 2 is a schematic view of a sampling gate position.

In step 100, parameters selected by user through a user interface are collected, wherein the parameters include information relating to the sampling gate position and selected PRF level. The information relating to the sampling gate position includes a sample volume depth (SVD), i.e., GateDepth in FIG. 2, and a sampling gate size, i.e., GateSize in FIG. 2. The sampling gate herein is the real sampling gate and the corresponding SVD is the real SVD. Additionally, the standard PRF value corresponding to the selected PRF level selected through the user interface is marked as usePRF.

In step 102, a selectable PRF range Prf_Low~Prf_High for optimization is set, wherein Prf_Low<=usePRF and Prf_High>=usePRF. The selectable PRF range can be directly set by user through a user interface, or automatically generated by an ultrasonic system.

For example, in one embodiment, the selectable PRF range can be set by multiplying the standard PRF value corresponding to the selected PRF level by a preset upper limit parameter and a preset lower limit parameter respectively. For example, in one embodiment, Prf_Low=$\alpha$*usePRF Prf_High=$\beta$*usePRF where $\alpha$ and $\beta$ are the lower limit and upper limit parameters respectively preset by the system, and $\alpha<=1$, $\beta>=1$. The lower limit and upper limit parameters mainly affect the optimized adjustment range of each PRF level. They can be determined based on user's demand and the effect of image optimization.

In one embodiment, the selectable PRF range can be set by subtracting and adding the standard PRF value corresponding to the selected PRF level by preset adjustment parameters respectively. For example, in one embodiment, Prf_Low=usePRF−$a$ Prf_High=usePRF+$b$ where a and b are the PRF adjustment parameters respectively preset by the system, and a>=0, b>=0. The parameters mainly affect the optimized adjustment range of each PRF level. They can be determined based on user's demand and the effect of image optimization.

In the aforesaid embodiments, according to user's demand, the parameters $\alpha$, $\beta$, a and b may be directly set by user through a user interface, or automatically set by default by an ultrasonic system.

A plurality of methods for setting a selectable PRF range is described in the aforesaid embodiments. It will be understood by those skilled in the art that other methods can be utilized based on actual conditions, user demands, and the effect of image optimization. The methods for setting the PRF range mentioned in the above embodiments are exemplary and should not be construed as limiting.

Figure 3:
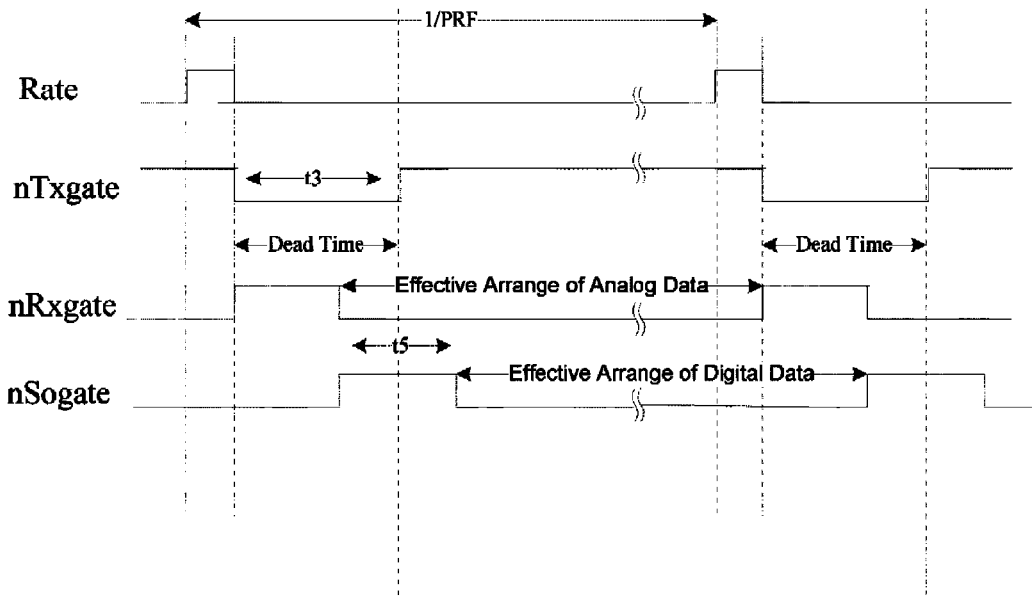
FIG. 3 is a timing diagram showing a period of dead time.

FIG. 3 shows a time series and the positions of dead time of ultrasonic pulse transmission and reception, wherein Rate means the beginning of each transmission and reception cycle, and nTxgate is a transmission time series. The effective time T3 of transmission in each cycle is a dead time. The time interval between two adjacent Rate is a repeat time interval PRI=1/PRF of transmission corresponding to the current transmitting PRF. Under the HPRF mode, if the time of the target signal at the current SVD returns to the probe is just falling in the dead time or very close to the dead time, the receiving of the target signal may meet obstacles or interferences, which reduces the SNR of Doppler spectral information.

If the sampling line of HPRF is determined, the emission order of each transducer in the probe and the relative time delay can be determined. Thus the transmitting effective time T3 in the time series can be determined. In actual use, the time length of dead time may be the effective time of transmission added by an additional moment, that is:

DeadTime=$T_3$+AdditionalDeadTime where the AdditionalDeadTime is the additional dead time which is a fixed value preset in the system. The fixed value is related to the method for designing the time series in the system and the performance of hardware used for emission.

The system calculates the times of the target signal returns to the probe at the beginning and end sampling gate positions, for example:

$$GateStart = \frac{2(GateDepth - GateSize/2)}{c} + DeadTime$$

$$GateEnd = \frac{2(GateDepth + GateSize/2)}{c} + DeadTime$$

wherein c is the velocity of sound in the tissue.

The number of dead time then is:

GateNumber=GateEnd*Prf_Low

An upper limit parameter of the number of dead time set in the system is MaxGateNumber. The parameter, which corresponds to the maximum number of sampling gates under HPRF mode, can be set based on the user's demand or the desired image effect. When the calculated GateNumber is equal to or larger than the upper limit parameter, GateNumber and usePRF may be adjusted in a forcible manner as follow:

$$GateNumber = MaxGateNumber - \varepsilon$$

$$usePRF = \frac{GateNumber}{GateEnd}$$

where $\varepsilon$ is a fixed parameter set in the system. The parameter is usually set as a small value and can be adjusted with image effect.

Due to the size of sampling gate, the time of each depth of the sampling gate is GateStart~GateEnd corresponding from emission to reception. To eliminate the interference from dead time, the GateStart cannot be fallen in the previous adjacent dead time and the GateEnd can not be in the next adjacent dead time. Accordingly, in one embodiment, the selectable PRF range is restricted by the current sampling gate may be:

$$GatePrf\_Low = \frac{\text{fix}(GateNumber)}{GateStart - DeadTime}$$

$$GatePrf\_High = \frac{\text{fix}(GateNumber) + 1}{GateEnd}$$

wherein fix means rounding a number to the nearest integer.

The real emission PRF range should be in the selectable PRF range restricted by the sampling gate, such that:

Temp_Prf_Low=max(GatePrf_Low,Prf_Low)

Temp_Prf_High=min(GatePrf_High,Prf_High)

If Temp_Prf_Low<=Temp_Prf_High, an effective PRF can be searched in the adjustment range by the system; otherwise, the system fails to search the effective PRF and the sampling gate size must be reduced (step 104).

Additionally, after reducing the sampling gate size, a new judgment is needed based on the reduced sampling gate until a suitable size of the sampling gate is searched or the size is adjusted to the minimum sampling gate size restricted by the system.

The system evaluates (step 106) each PRF successively selected from the selectable PRF range with a preset step. The step Prf_Step may be set flexibly according to the user's demand, the effect of image optimization, or the time and resource spent on evaluation.

The system then takes the PRF evaluated currently as Prf_temp and calculates the corresponding number of dead time with, for example, the following formula:

GateNumber=GateEnd*Prf_temp

If GateNumber>=MaxGateNumber, the Prf_temp fails to meet the requirement and the total score of Prf_temp is set with a worst score (i.e., set to zero, that is Score=0); if GateNumber<MaxGateNumber, scoring the Prf_temp (step 106). The scoring may contain three scoring items: the scoring distance to the previous adjacent dead time, the scoring distance to the next adjacent dead time, and the scoring similarity with the standard PRF value corresponding to current PRF level. The three steps will be further specifically described herein.

1. Scoring Distance to the Previous Adjacent Dead Time

The time distance from a beginning time to the previous dead time may be as follow, where the beginning time is the one at which the signal at the beginning position of sampling gate returns to the probe $$DisStart = GateStart - \frac{\text{fix}(GateNumber)}{\text{Prf\_temp}} - DeadTime$$

The score may be function of the time distance. The larger the time distance, the better the score.

2. Scoring Distance to the Next Adjacent Dead Time

The time distance from an end time to the next dead time may be as follows, wherein the end time is the one at which the signal at the end position of sampling gate returns to the probe:

$$DisEnd = \frac{\text{fix}(GateNumber) + 1}{\text{Prf\_temp}} - GateEnd$$

The score may be function of the time distance. The larger the time distance, the better the score.

3. The Scoring Similarity with the Standard PRF Value Corresponding to Current PRF Level Comparing the difference between the PRF evaluated currently and the standard PRF value corresponding to the current PRF level, the similarity is the function of difference. The smaller the difference, that is, Prf_temp is closer to use PRF, the better the score.

4. Total Score

After obtaining three scoring items, the final score may be function of one of the three items (including the case where the score is one item itself, which is also called as the function of the item in the disclosure), or any two of the three items (i.e., the product of any two items), or the function of the three items (i.e., the product of the three scoring items); wherein the final score function can be set flexibly, for example, it can be each item itself, or can be other functions.

Among the aforesaid selectable PRF range, the PRF with best total score is taken as the best PRF of the current PRF level. The size of the sampling gate after adjustment is output at the same time. The scoring of PRF is then finished.

It will be understood by those skilled in the art that the definition of "the best" or "the worst" may be defined flexibly and is not limited in the disclosure. For example, "the best" can be defined as the higher score and "the worst" as the lower score; alternatively, "the best" can be defined as the lower score and "the worst" as the higher score.

Additionally, besides the above-mentioned three score items, the score items may be other which can measure the performance of current Prf_temp as understood by those skilled in the art. The scoring methods are not limited in the three score items. They may be any score items which can be used to evaluate the performance of current Prf_temp.

After obtaining the best PRF, the number of virtual sampling gates and their corresponding SVD can be calculated with the current real SVD as follows:

$$\frac{2*SVD_{real}}{c} - \frac{2*SVD_{dummy}}{c} = \frac{k}{PRF}, k = 1, 2, \ldots, m-1$$

If the lightest SVD of the virtual sampling gate is smaller than a threshold DepthThre, the current PRF level is not suitable. The next PRF level is should be scored to search for the best PRF corresponding to next PRF level (step 108). The threshold DepthThre is preset and may be flexibly adjusted based on actual image effect.

Figure 4:
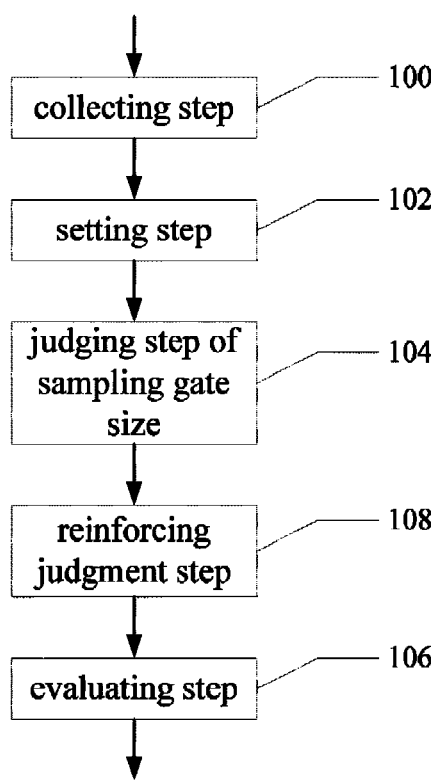
FIG. 4 is a flowchart of method for HPRF Doppler ultrasonic imaging.

In another embodiment, as shown in FIG. 4, the reinforcing judgment step 108 and the evaluating step of PRF 106 may be interchanged. That is, the reinforcing judgment step may be performed by utilizing the standard PRF value of the current level so as to determine whether to adjust the level. After searching the suitable level, the method may proceed to the evaluating step to search for the best PRF value corresponding to the level, and set the best PRF to be the PRF utilized in transmitting ultrasonic pulses in the system. In this case, the selected PRF is adopted in the aforesaid formulas about the depth of each virtual sampling gate.

In each of the aforesaid embodiments, there are a plurality of preset parameters. These parameters may be set flexibly according to actual situations. They may be directly set by a user through a user interface, or may be set by default by an ultrasonic system.

Figure 5:
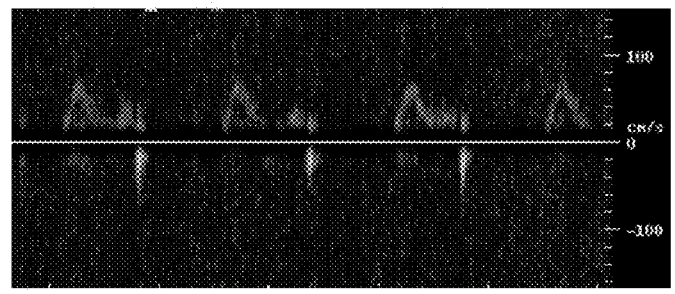
FIG. 5 shows Doppler spectrograms before and after automatic optimization of PRF emitted under HPRF mode.
Figure 5:
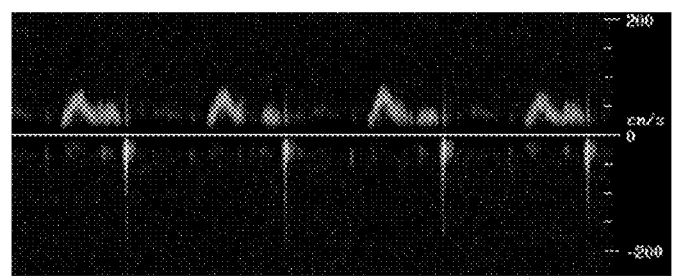

By means of the aforesaid process of PRF automatic optimization, the time required for the signal to return to the probe from target position is effectively not fallen into or close to the range of dead time, thus avoiding a low SNR of the Doppler spectrum. FIG. 5 shows the image before and after optimization, wherein FIG. 5*a* is the Doppler spectrum before optimization and FIG. 5*b* is the optimized Doppler spectrum. From FIG. 5, after HPRF is optimized, the Doppler signals are markedly enhanced, the SNR is improved, and the contour of the velocity information is more clearly shown.

Figure 6:
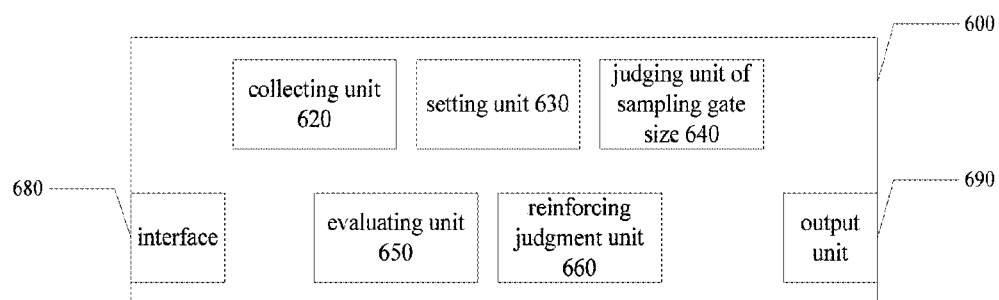
FIG. 6 is a schematic block diagram of an apparatus for HPRF Doppler ultrasonic imaging.

FIG. 6 illustrates an apparatus 600 for HPRF Doppler ultrasonic imaging according to one embodiment. The apparatus 600 may include a collecting unit 620, a setting unit 630, and an evaluating unit 650. In other embodiments, the apparatus 600 optionally further includes a judging unit of sampling gate size 640 and/or a reinforcing judgment unit 660. In one embodiment, the collecting unit 620 is configured to implement step 100 of FIG. 1; the setting unit 630 is configured to implement step 102; the judging unit of sampling gate size 640 is configured to implement step 104; the evaluating unit 650 is configured to implement step 104; and the reinforcing judgment unit 660 is configured to implement step 108.

In one embodiment, the apparatus 600 for HPRF Doppler ultrasonic imaging optionally further includes an interface 680 and an output unit 690. The interface 680 may be configured to collect the information selected by the user, i.e., PRF level, SVD, and the sampling gate size. The output unit 690 may be configured to output the best PRF value.

Figure 7:
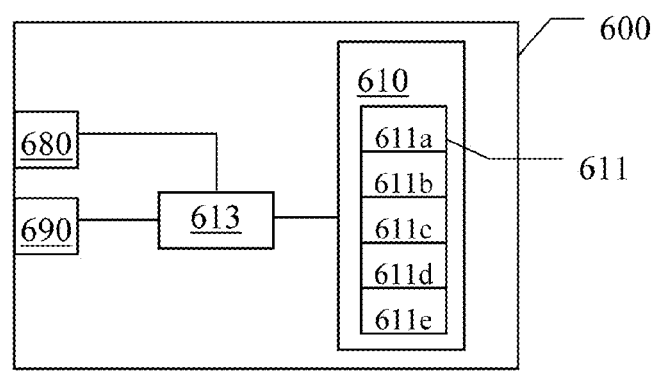
FIG. 7 is a schematic block diagram of an apparatus for HPRF Doppler ultrasonic imaging.

According to another embodiment shown in FIG. 7, the apparatus 600 for HPRF Doppler ultrasonic imaging comprises a processing unit 613, i.e., DSP or CPU. The processing unit 613 may be a single unit or a plurality of units for implementing the above-mentioned steps. Additionally, the apparatus optionally further includes an interface 680 and an output unit 690. Moreover, the apparatus 600 further comprises at least one non-transitory computer-readable medium 610 which may be in form of non-volatile memory, i.e., EEPROM, flash or disk drive. The computer-readable medium 610 may include a computer program 611 including program codes, which, when executed by the processing unit 613, implements the steps shown in FIG. 1 and/or FIG. 4.

The computer program 611 in the apparatus 600 may include a collecting module 611*a* for implementing step 100, a setting module 611*b* for implementing step 102, a judging module of sampling gate size 611*c* for implementing step 104, an evaluating module 611*d* for implementing step 106, and a reinforcing judgment module 611*e* for implementing step 108. In other words, when running the modules 611*a*-611*e* on the processing unit 613, the modules respectively correspond to the units 620, 630, 640, 650, 660 shown in FIG. 6.

Figure 8:
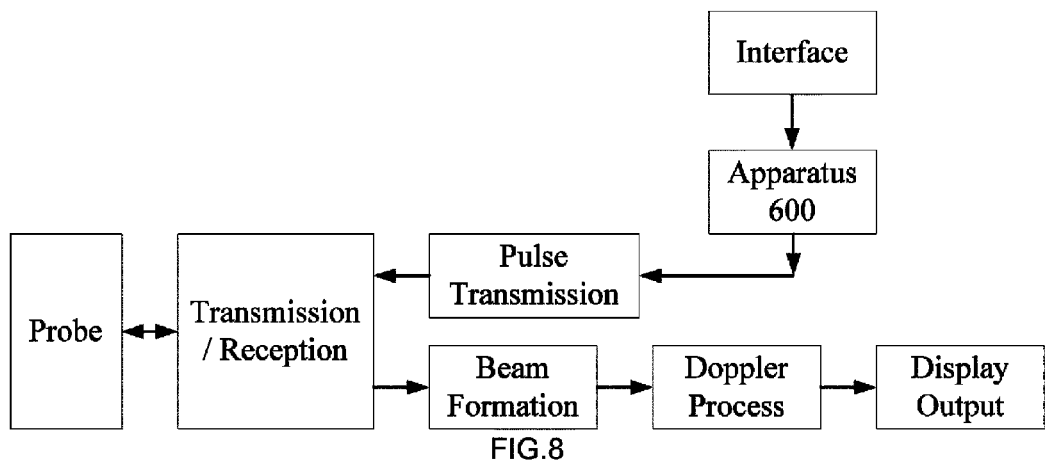
FIG. 8 is a schematic block diagram of a Doppler ultrasonic imaging system including an apparatus for HPRF Doppler ultrasonic imaging.

In one embodiment, the apparatus 600 for HPRF Doppler ultrasonic imaging can be realized in a Doppler ultrasonic imaging system with software, hardware, firmware, or their combination, as shown in FIG. 8.

Though present disclosure has been described in details by way of aforesaid embodiments, the invention is not limited by these embodiments. It can be understood by those skilled in the art that various modifications, equivalent substitutions, and changes can be made, which should be considered as within the protective scope of the invention defined by the attached claims. For example, the various steps or modules mentioned above may be divided into two or more steps or modules, or multiple steps or modules may be merged into one step or module. Additionally, the terms mentioned in the claims and/or descriptions are used for convenience and should not be construed as limiting. Further, the phrase "one embodiment" may represents different embodiments.

What is claimed is:

1. A method for determining a pulse repeat frequency (PRF) for use in a High Pulse Repeat Frequency (HPRF) Doppler ultrasonic imaging system, comprising:
   collecting parameters via a user interface including a selected PRF level, real sample volume depth, and sampling gate size;
   setting via a processing unit a selectable PRF range according to a standard PRF value corresponding to the selected PRF level;
   evaluating via the processing unit each PRF successively selected from the selectable PRF range with a preset step; and
   taking the PRF with best evaluation as the best PRF of the selected PRF level;
   using the best PRF of the selected PRF level in transmission of ultrasonic pulses.

2. The method of claim 1, further comprising:
   calculating a virtual sample volume depth based on the best PRF and current real sample volume depth, and judging whether the calculated virtual sample volume depth is smaller than a preset threshold; if the calculated virtual sample volume depth is smaller than the preset threshold, proceeding to a next PRF level to search for the corresponding best PRF with the setting step and the evaluating step, otherwise, the best PRF is utilized in ultrasonic pulses transmission.

3. The method of claim 1, wherein, before the evaluating step, the method further comprises:
   calculating a virtual sample volume depth based on the selected PRF and the current real sample volume depth, and judging whether the calculated virtual sample volume depth is smaller than a preset threshold; if the calculated virtual sample volume depth is smaller than the preset threshold, proceeding to next PRF level to reprocess the reinforcing judgment step, otherwise, proceeding to the evaluating step.

4. The method of claim 1, wherein the setting step comprises:
   setting the selectable PRF range by multiplying the standard PRF value corresponding to the selected PRF level by a preset lower limit parameter and an upper limit parameter respectively, wherein the lower parameter is less than or equal to 1, and the upper parameter is greater than or equal to 1.

5. The method of claim 1, wherein the setting step comprises: setting the selectable PRF range by subtracting and adding the standard PRF value corresponding to the selected PRF level by preset adjustment parameters respectively, wherein the adjustment parameter is greater than or equal to zero.

6. The method of claim 1, wherein the evaluating step comprises: if a dead-time number of the PRF evaluated currently is larger than or equal to a preset upper limit of dead-time number, the score of the PRF is set with a worst score, otherwise, the score of the PRF is a function of one or at least any two of the following three scoring items: a scoring distance to a previous adjacent dead time, a scoring distance to a next adjacent dead time, and a scoring similarity with the standard PRF value corresponding to a current PRF level.

7. The method of claim 6, wherein the scoring distance to the previous adjacent dead time is a function of the time distance from a beginning time to the previous dead time, wherein the beginning time is the one at which the signal at the beginning position of sampling gate returns to the probe; and wherein the greater the time distance, the better the score.

8. The method of claim 6, wherein the scoring distance to the next adjacent dead time is a function of the time distance from an end time to the next dead time, wherein the end time is the one at which the signal at the end position of sampling gate returns to the probe; and wherein the greater the distance, the better the score.

9. The method of claim 6, wherein a scoring similarity with the standard PRF value corresponding to the current PRF level is a function of the difference between the PRF evaluated currently and the standard PRF value corresponding to the current PRF level; and wherein the smaller the difference, the better the score.

10. An apparatus for High Pulse Repeat Frequency (HPRF) Doppler ultrasonic imaging, comprising:
 a processing unit; and
 a non-transitory computer readable medium storing program code modules executable by the processing unit, the modules comprising:
  a collecting module configured for collecting parameters from a user, the parameters including a selected PRF level, real sample volume depth, and sampling gate size;
  a setting module configured for setting a selectable PRF range according to a standard PRF value corresponding to the selected PRF level; and
  an evaluating module configured for evaluating each PRF successively selected from the selectable PRF range with a preset step;
  wherein the processing unit is to take the PRF with the best evaluation as the best PRF of the selected PRF level for use in ultrasonic pulses transmission.

11. The apparatus of claim 10, further comprising:
 a reinforcing judgment module configured for calculating virtual sample volume depth based on the best PRF and current real sample volume depth, and for judging whether the calculated virtual sample volume depth is smaller than a preset threshold; if the calculated virtual sample volume depth is smaller than the preset threshold, proceeding to next PRF level to search the corresponding best PRF with the setting module and the evaluating module, otherwise, the best PRF is utilized in ultrasonic pulses transmission.

12. The apparatus of claim 10, further comprising:
 a reinforcing judgment module configured for calculating virtual sample volume depth based on the selected PRF and current real sample volume depth, judging whether the calculated virtual sample volume depth is smaller than a preset threshold; if the calculated virtual sample volume depth is smaller than the preset threshold, proceeding to next PRF level to reprocess the reinforcing judgment module, otherwise, proceeding to the evaluating module.

13. The apparatus of claim 10, wherein the setting module is configured to set the selectable PRF range by multiplying the standard PRF value corresponding to the selected PRF level by a preset lower parameter and upper parameter, wherein the lower parameter is smaller than or equal to 1, and the upper parameter is larger than or equal to 1.

14. The apparatus of claim 10, wherein the setting module is configured to set the selectable PRF range by subtracting the standard PRF value corresponding to the selected PRF level with a preset adjustment parameter, wherein the adjustment parameter is larger than or equal to zero.

15. The apparatus of claim 10, wherein, if a dead-time number of the PRF evaluated currently is larger than or equal to a preset upper limit of dead-time number, the score of the PRF is set with a worst score, otherwise, the score of the PRF is a function of one or at least any two of the following three scoring items: the scoring distance to the previous adjacent dead time, the scoring distance to the next adjacent dead time, and the scoring similarity with the standard PRF value corresponding to current PRF level.

16. A Doppler ultrasonic imaging system comprising the apparatus of claim 10.

* * * * *